United States Patent
Berry et al.

(10) Patent No.: US 8,038,006 B2
(45) Date of Patent: Oct. 18, 2011

(54) BLISTER-TYPE PACKAGING FOR INHALERS

(75) Inventors: Simon Berry, Loughborough (GB); Len Brookhouse, Macclesfield (GB)

(73) Assignee: AstraZeneca, Sodertalie (SE)

( * ) Notice: Subject to any disclaimer, the term of this patent is extended or adjusted under 35 U.S.C. 154(b) by 0 days.

(21) Appl. No.: 12/266,815

(22) Filed: Nov. 7, 2008

(65) Prior Publication Data
US 2009/0139888 A1 Jun. 4, 2009

Related U.S. Application Data

(60) Provisional application No. 60/986,656, filed on Nov. 9, 2007.

(51) Int. Cl.
*A61B 17/06* (2006.01)
(52) U.S. Cl. ......... 206/438; 206/471; 206/470; 206/363
(58) Field of Classification Search .......... 206/363, 206/438, 570, 461, 467, 470, 471, 463; 220/4.22, 220/4.23, 4.24; 204/204, 232
See application file for complete search history.

(56) References Cited

U.S. PATENT DOCUMENTS

| | | | | |
|---|---|---|---|---|
| 3,111,220 A * | 11/1963 | Bostrom | ........................ | 206/539 |
| 3,116,825 A * | 1/1964 | Thomas | ........................ | 206/471 |
| 3,127,993 A * | 4/1964 | Phipps | ........................ | 206/484 |
| 3,645,384 A * | 2/1972 | Wind | ........................ | 206/471 |
| 3,776,375 A * | 12/1973 | Rohdin | ........................ | 206/459.5 |
| 4,169,531 A * | 10/1979 | Wood | ........................ | 206/531 |
| 4,375,262 A * | 3/1983 | Hrenyo | ........................ | 206/418 |
| 4,512,474 A * | 4/1985 | Harding | ........................ | 206/461 |
| 4,619,364 A * | 10/1986 | Czopor, Jr. | ........................ | 206/379 |
| 4,669,610 A * | 6/1987 | Lindsey et al. | ........................ | 206/320 |
| 4,681,223 A * | 7/1987 | Roberts | ........................ | 206/354 |
| 4,958,731 A * | 9/1990 | Calcerano | ........................ | 206/705 |
| D320,934 S * | 10/1991 | Cross et al. | ........................ | D9/415 |
| 5,090,570 A * | 2/1992 | Todd | ........................ | 206/463 |
| 5,129,516 A * | 7/1992 | Theros | ........................ | 206/463 |
| 5,176,634 A * | 1/1993 | Smith et al. | ........................ | 604/87 |
| 5,322,161 A * | 6/1994 | Shichman et al. | ........................ | 206/204 |
| 5,358,113 A * | 10/1994 | Hellenbrand | ........................ | 206/411 |
| 5,485,919 A * | 1/1996 | Samberg et al. | ........................ | 206/461 |
| 5,560,490 A * | 10/1996 | Chawla | ........................ | 206/539 |
| 5,642,810 A * | 7/1997 | Warner et al. | ........................ | 206/389 |
| 5,871,097 A * | 2/1999 | Shida et al. | ........................ | 206/521 |
| 7,398,879 B2 * | 7/2008 | Nottingham et al. | ........................ | 206/349 |
| 2002/0175164 A1* | 11/2002 | Dees et al. | ........................ | 220/4.24 |
| 2006/0144735 A1* | 7/2006 | Baker | ........................ | 206/438 |
| 2007/0023884 A1 | 2/2007 | Branzell | | |
| 2007/0102317 A1* | 5/2007 | Crawford et al. | ........................ | 206/470 |

FOREIGN PATENT DOCUMENTS

| | | |
|---|---|---|
| WO | WO 99/27813 | 6/1999 |
| WO | WO 2006/003386 | 1/2006 |

* cited by examiner

*Primary Examiner* — David Fidei
(74) *Attorney, Agent, or Firm* — Finnegan, Henderson, Farabow, Garrett & Dunner, L.L.P.

(57) ABSTRACT

A dispensing device package including a protective enclosure containing a dispensing device, e.g. an inhaler. The protective enclosure includes at least one rigid enclosure member, which in some implementations defines a recess to house a section of the dispensing device.

11 Claims, 11 Drawing Sheets

BLISTER-TYPE PACKAGING FOR INHALERS

This application claims the benefit of the filing date of U.S. Provisional Application No. 60/986,656, which was filed on Nov. 9, 2007. The contents of U.S. Application No. 60/986,656 are incorporated by reference in their entirety as part of this application.

TECHNICAL FIELD

The invention relates to medicinal dispensing device packaging, such as a package for containing, for example, a pressurized metered dose inhaler (hereinafter referred to as a "pMDI"), a dry powder inhaler (DPI), or a nasal inhaler.

BACKGROUND pMDIs are well known in the art of inhalation devices. It is therefore not necessary to describe the construction and operation of a pMDI other than in bare essentials.

A pMDI includes a canister unit and a housing. The housing is generally tubular and formed of a plastic material, for instance by molding. The canister unit includes a canister having one open end, typically made from a metal such as aluminum. The open end of the canister is sealingly capped by a metering valve assembly. The valve assembly includes a hollow dispensing member, usually in the form of a valve stem, which projects from the open end of the canister. Actuation of the metering valve assembly results in a metered dose of the aerosol formulation being dispensed from the canister through the valve stem.

In use, the sealed canister contains a pressurized medicinal aerosol formulation. The formulation includes the medicament and a fluid propellant, and optionally one or more excipients and/or adjuvants. The medicament is typically in solution or suspension in the formulation.

The housing includes an internal passageway having an open end. A nozzle block, is arranged to receive the valve stem from the canister unit, and to direct the dispensed metered dose to a mouth piece (or nasal piece). In use, a patient in need of a metered dose of the medicinal aerosol formulation concurrently inhales on the mouthpiece and actuates the canister unit. The inspiratory airflow produced by the patient entrains the metered dose of the medicinal aerosol formulation into the patient's respiratory tract.

Dispensing devices are commonly stored in a sealed protection pouch inside a package housing such as a cardboard box or the like. Depending on the type of dispensing device and requirements related thereto, the protection pouch may be arranged to keep the dispensing device protected from moisture, contamination, and/or dust. The protection pouch is commonly made from a thin flexible material such as plastic film, coated paper, metal foil, laminates thereof or the like. Mechanical protection of the dispensing device is mainly provided by the package housing. Moreover, the dispensing device and the protection pouch are normally free to move about inside the package housing.

It has been concluded that current protection pouch designs may be susceptible to punctures due to fatigue failure in the materials and due to impacts from sharp edges on the inhaler. Fatigue failure frequently occurs at crease points in the pouch, where the material is worn and work hardened during vibration. The pouch material punctures in the lower portion of the pouch, generally close to the sides and at evident fold points in the foil. This failure is caused by the vertical movement of the pouch and contents within the product carton during handling, transport, etc, whereby the foil pouch e.g. flexes at natural folds.

WO 2006/003386 discloses a package for a dispenser in the form of an inhaler, comprising a support said to be arranged to suspend the dispenser in order to avoid unintentional actuation. Several types of suspension arrangements are proposed, all said to be arranged to allow a controlled suspended movement of the inhaler inside the package. However, there are no specific provisions for avoiding punctures of the sealed pouch.

SUMMARY

In one implementation, a dispensing device package includes a protective enclosure containing a dispensing device, e.g. an inhaler. The protective enclosure includes at least one rigid enclosure member, which in some implementations defines a recess to house a section of the dispensing device. In some implementations, the recess has a shape resembling the dispensing device. In some implementations, the section of the dispensing device housed in the recess includes the entire dispensing device.

In some implementations, the protective enclosure further includes an essentially flat enclosing lid attached to the rigid enclosure member. Further, the recess, in some implementations, has a depth essentially equal to the smallest dimension or the largest dimension of the dispensing device.

In some implementations, the rigid enclosure member includes two rigid enclosure members attached to each other, each defining a recess to house a respective section of the dispensing device. In some implementations, each recess has a shape resembling the respective section of the dispensing device. Further, in some implementations the dispensing device is an inhaler having an elongated main body and a mouth piece extending in an essentially transverse direction with respect to the main body. Further, the section of the dispensing device housed within the recess defined by one of the two rigid enclosure members includes essentially the whole mouth piece. In some implementations, the two rigid enclosure members are attached to each other in a plane that is essentially parallel with a longitudinal direction of the main body, and diagonal to the transverse direction in which the mouth piece extends. In some implementations, the two rigid members is formed from one sheet of rigid material that is folded.

In some implementations, the dispensing device package also includes at least one support member arranged to support the dispensing device. Further, in some implementations, the support member is integrally formed in the recess of at least one of two rigid enclosure members. Some implementations of the dispensing device package also include one or more auxiliary features selected from a desiccant member, a patient information leaflet, a spare mouth piece, and a spare canister. In some implementations, the rigid enclosure member is an essentially flat back plate and the protective enclosure includes a flexible sheet attached to the back plate. In some implementations, the protective enclosure is arranged in a box. In some implementations, the rigid enclosure member is coated with a functional layer including a barrier coating reducing gas and moisture permeability of the protective enclosure and/or a radiation protection coating. In some implementations, the rigid enclosure member is planar and defines a cutout accommodating the dispensing device. The dispensing device lies in the plane of the rigid member, which surrounds the dispensing device.

The package described herein may be able to vastly lower the risk for punctures of the protection enclosure containing the dispensing device.

The details of one or more examples of the invention are set forth in the accompanying drawings and the description below. Other features, objects, and advantages of the invention will be apparent from the description and drawings, and from the claims.

BRIEF DESCRIPTION OF DRAWINGS

Like reference symbols in the various drawings indicate like elements.

DETAILED DESCRIPTION

Figure 1:
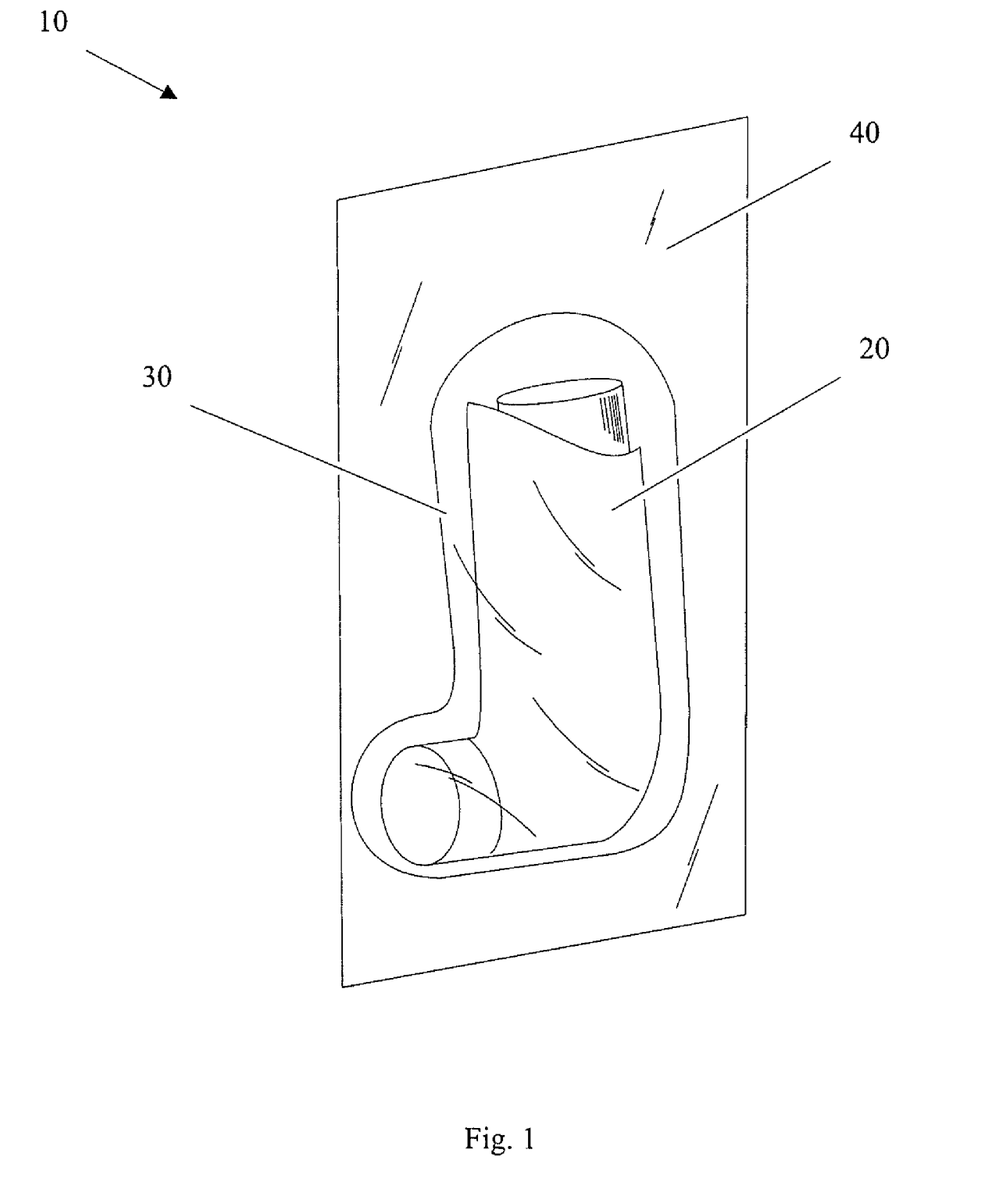
FIG. 1 is a schematic perspective view of one example of a package.

FIG. 1a is a schematic perspective view of an example of a package 10 for a dispensing device 20, in the form of a pMDI. The package 10 includes a protective enclosure 30 in which the dispensing device 20 is housed. In order to provide enhanced support and protection for the dispenser 20, the protective enclosure 30 includes at least one rigid enclosure member 40. Throughout this description, the term enclosure member is defined as a member of the protective enclosure that constitutes at least a section of the inner wall of the enclosed protection cavity, as will be evident from the descriptions of the examples below. Moreover the term rigid enclosure member refers to a member formed of a material or formed in way, such that it provides structural rigidity to the protective enclosure 30. Hence, the rigid enclosure member 40 may include any suitable rigid material such as plastic, cardboard, metal, etc, or combinations of the same, or of any flexible material such as paper, rubber, foils and laminates of the above materials. In some examples, the rigid enclosure member 40 includes a plastic sheet or plastic laminate sheet that is given the desired shape by any suitable forming technique. In another example, the rigid enclosure member 40 includes a metal, e.g. aluminum, that is deep drawn or the like to the desired shape. In yet another example, the rigid enclosure member 40 includes a coated cardboard sheet.

Figure 11:
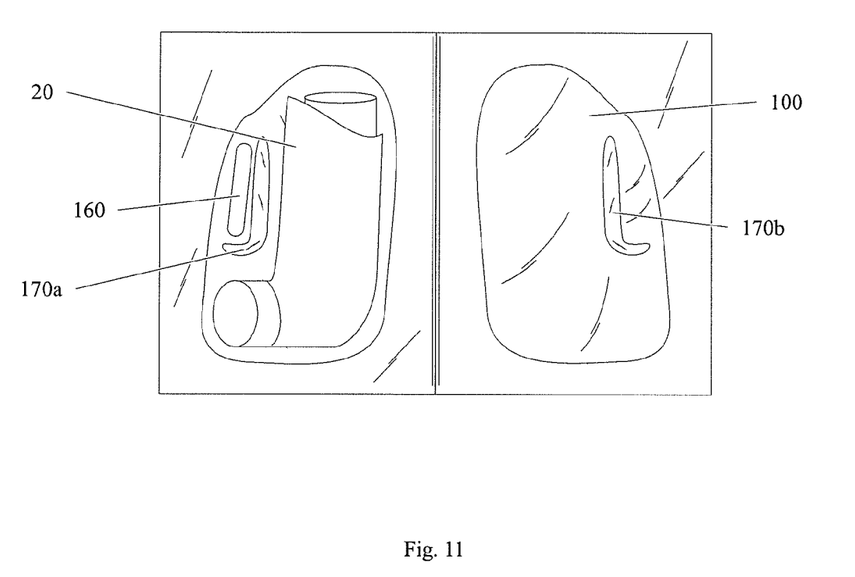
FIG. 11 shows an example of a protective enclosure and a package.

In each of the disclosed examples, with the exception of FIG. 11, the package 10 is shown containing one single dispensing device 20. However, the package 10 may be formed to house one or more dispensing devices 20 in one or more enclosures 30. In addition, in some examples, the enclosure 30 includes spaces or areas where auxiliary features, such as a desiccant, a spare mouth piece, a spare medicament canister, or a patient insert, may be added.

Figure 2:
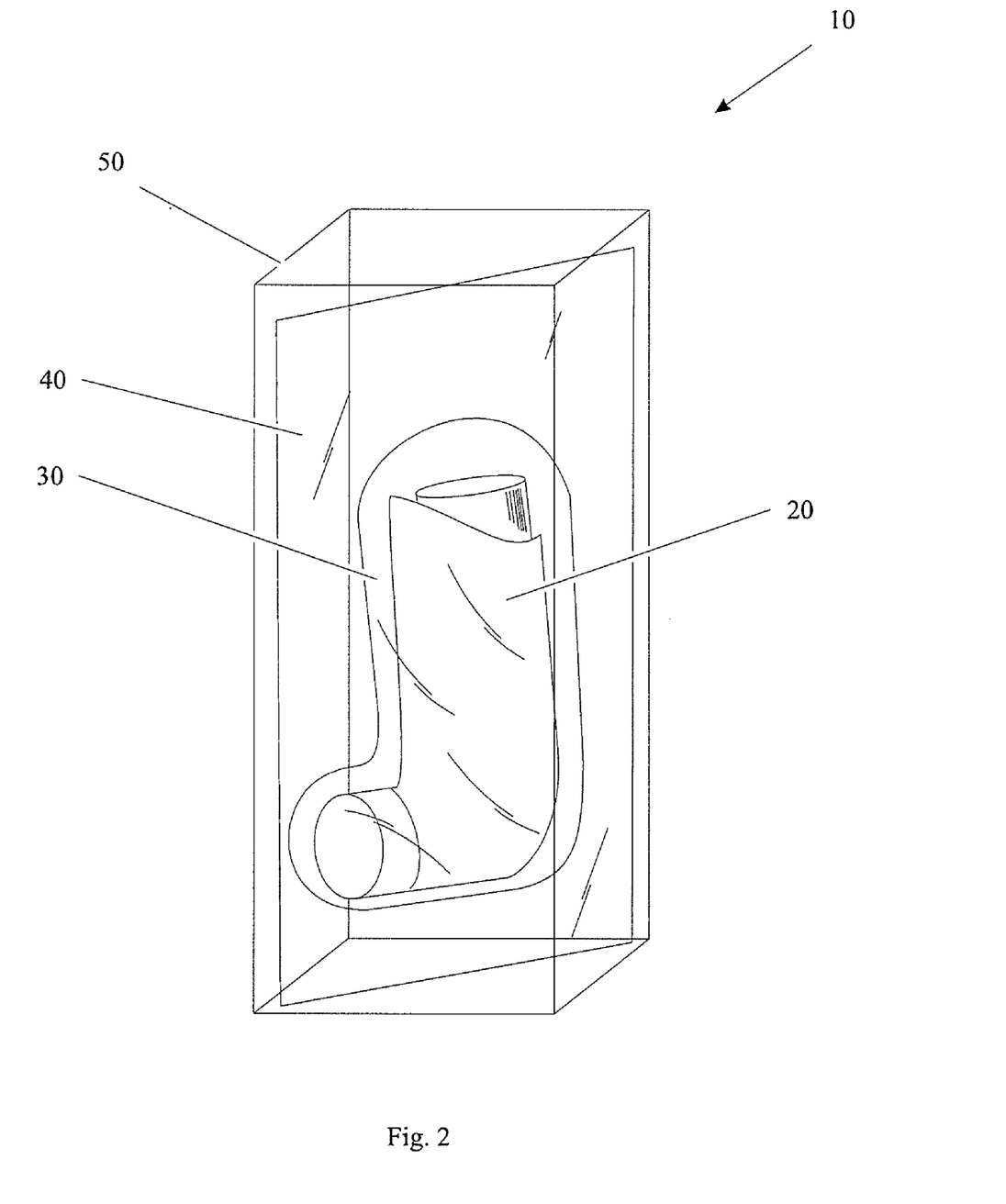
FIG. 2 is a schematic perspective view of the package of FIG. 1 arranged in a box.

As shown in the example of FIG. 2, the protective enclosure 30 containing the dispenser is arranged inside a box 50. The box 50 may be of many different shapes and of different size depending on the dispensing device 20 to be contained therein. Examples of shapes include a classic brick type, a tetrahedron type, and a tube type, as well as any other suitable shape. The box 50 may be formed from a large selection of materials that provide sufficient rigidity, such as cardboard, plastic, metal etc. The box 50 mainly serves to facilitate handling of the package 10 and to provide display surfaces on which informative and display information can be printed.

As is discussed above, the protection enclosure 30 may include any suitable barrier materials such as the enclosure materials discussed below. In addition, as will be discussed more in detail below, parts of the protection enclosure 30 may include different materials. There are numerous ways of forming the protection enclosure 30 and possible forming processes will not be discussed in full detail herein. Moreover, depending on the enclosure materials, there are numerous ways of closing and if required sealing the protection enclosure 30 such as by heat or friction welding, by use of a suitable adhesive, mechanical lock mechanisms or the like. In some examples, the enclosure material may be coated with a functional layer either before or after forming to the desired shape. Examples of such functional layers include barrier coatings that reduce the gas and moisture permeability, such as diamond like carbon coating or parylene, radiation protection coatings, such as UV filtering coatings, etc.

Figure 3A:
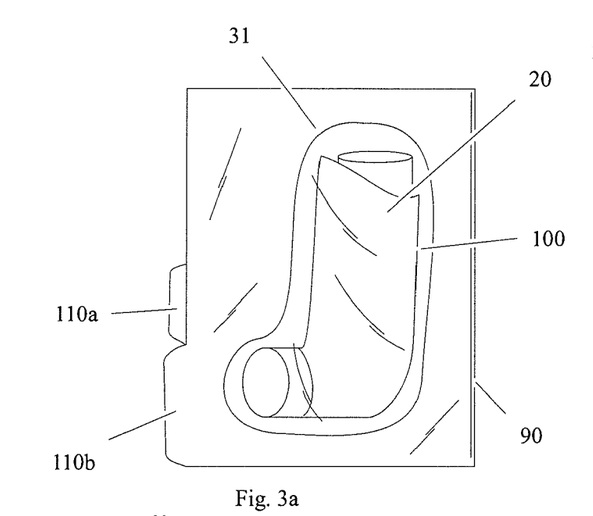
FIGS. 3a to 3d show one example of a protective enclosure and a package.
Figure 3B:
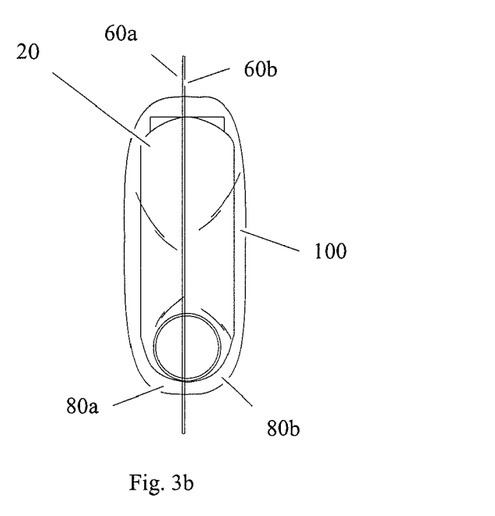
Figure 3C:
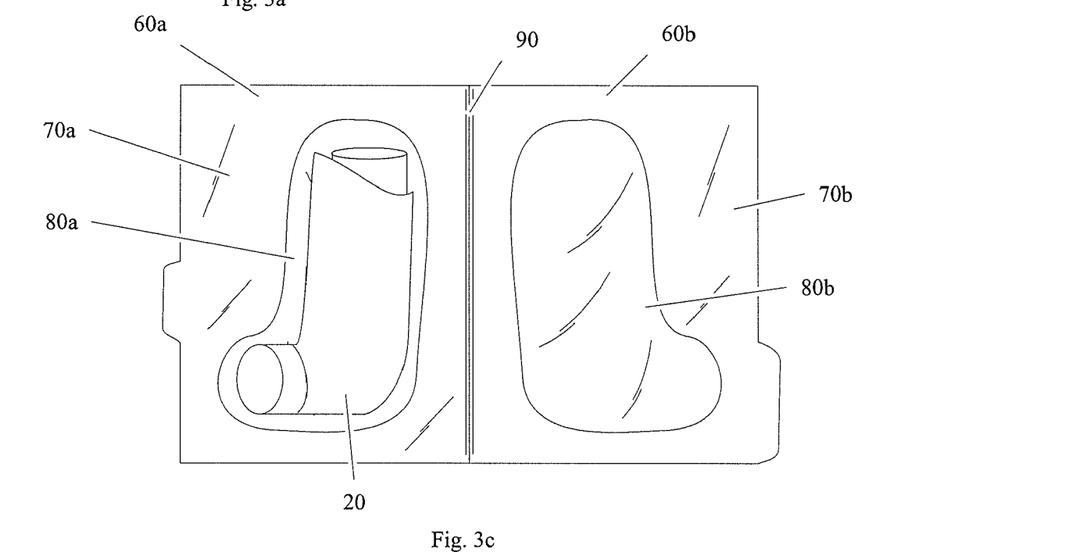
Figure 3D:
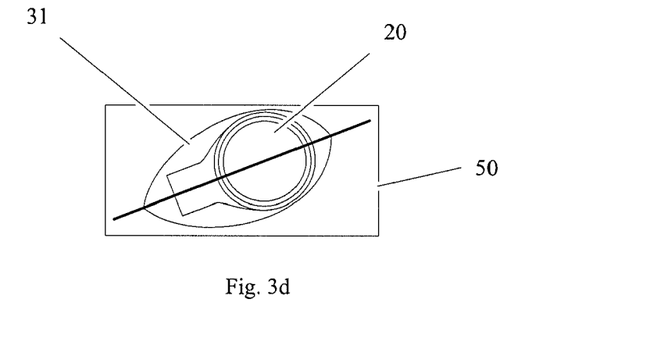
Figure 4A:
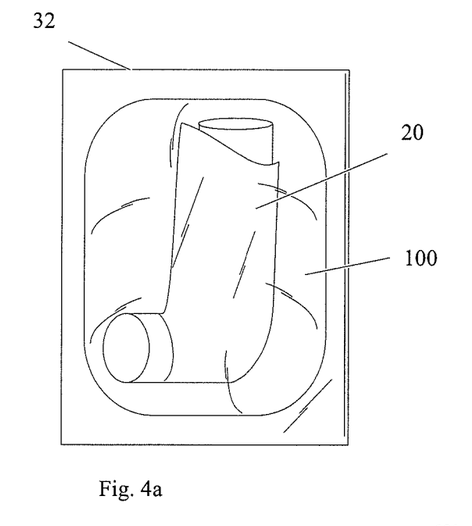
FIGS. 4a to 4d show one example of a protective enclosure and a package.
Figure 4B:
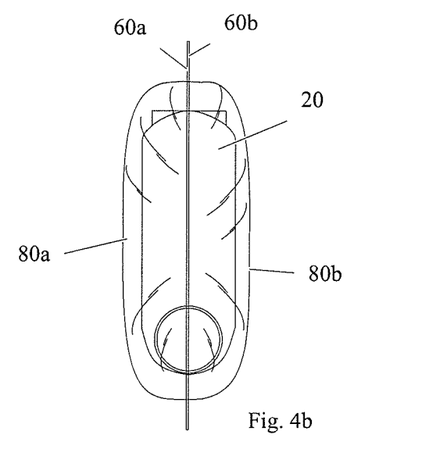
Figure 4C:
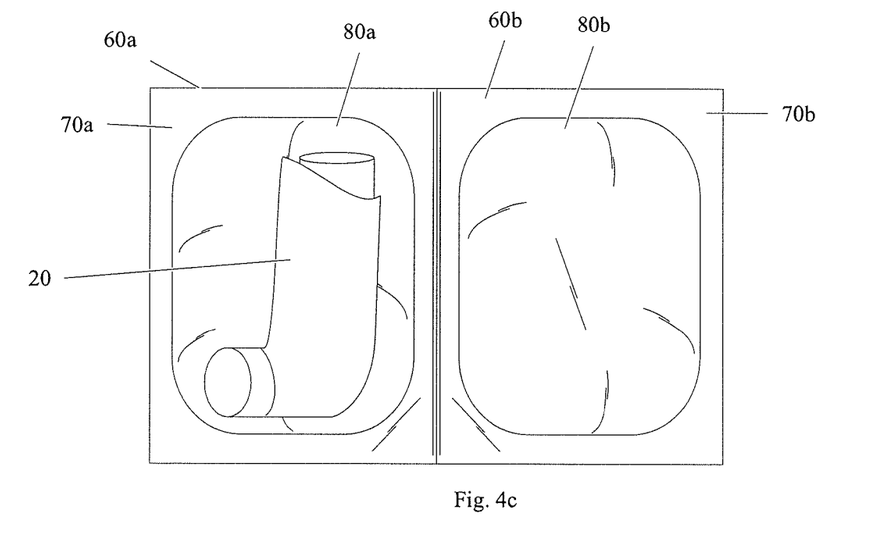
Figure 4D:
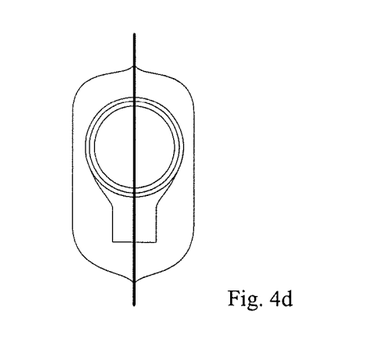
Figures 5A, 5B:
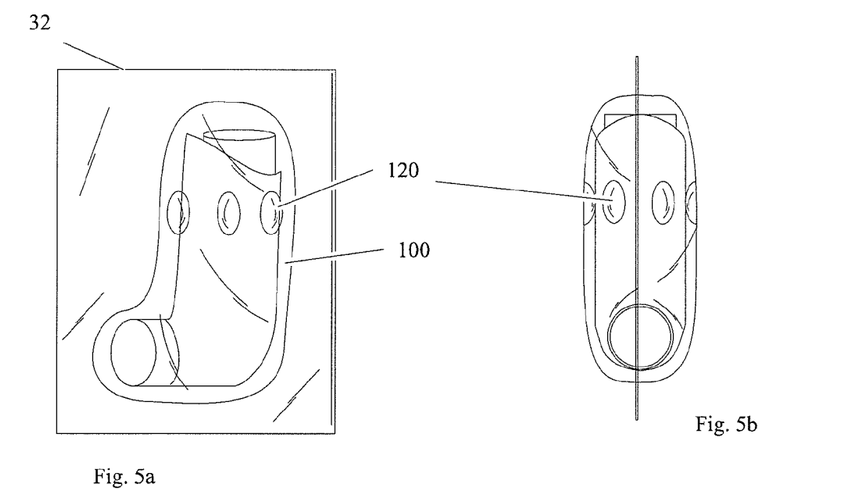
FIGS. 5a to 5d show one example of a protective enclosure and a package.
Figure 5C:
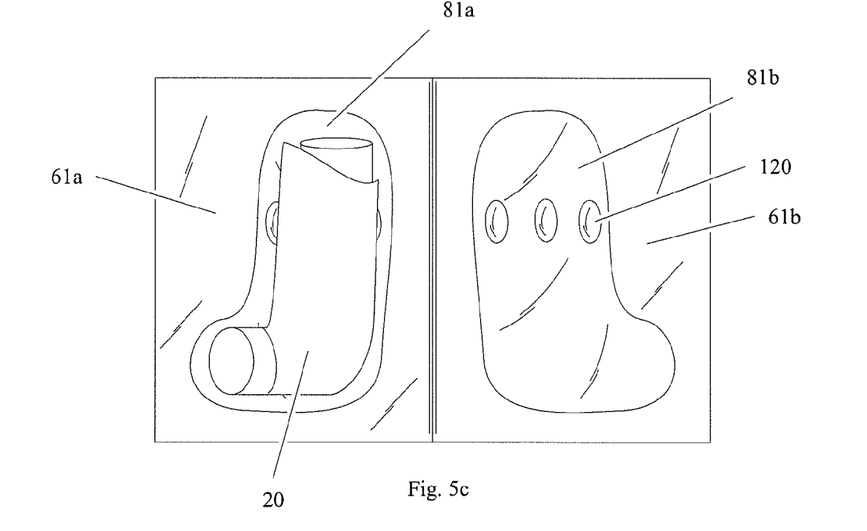
Figure 5D:
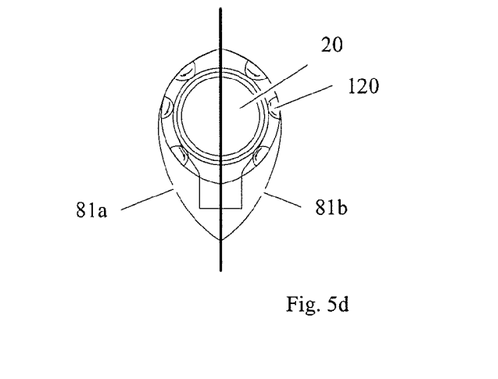

FIGS. 3a to 3d show one example of a protective enclosure 31 containing a dispensing device 20. FIG. 3a shows a front view and FIG. 3b a side view of the protective enclosure 31. FIG. 3c shows an unassembled protective enclosure 31 with a dispensing device arranged in position. FIG. 3d shows a top view of the assembled protective enclosure 31 arranged in a box 50 as shown in FIG. 2. As shown in FIG. 3c, the protective enclosure 31 is formed by two rigid enclosure members 60a and 60b, each having a flat rim 70a and 70b surrounding a recess 80a and 80b formed to house a section of the dispensing device 20, respectively. In the disclosed example, the rigid enclosure members 60a and 60b are shown as one integral member arranged to be folded along the hinge line 90 to be closed. After folding, the two rigid enclosure members 60a and 60b are attached/sealed to each other by any suitable technique as discussed above. However, the rigid enclosure members 60a and 60b could also be provided as independent members and attached/sealed accordingly.

In this example, each rigid enclosure member 60a and 60b is provided with an opening tab 110a and 110b, respectively. Tabs 110a and 110b are used to tear the protective enclosure 31 open by separation of the two rigid enclosure members 60a and 60b. In alternative examples, the opening procedure might involve cutting or tearing one or both of the rigid enclosure members 60a and 60b.

In the assembled state, the two recesses 80a and 80b form a protection cavity 100 adapted for containing the dispensing device 20. The two recesses 80a and 80b are of essentially complementary shape, and the protection cavity 100 has a shape that resembles the shape of the dispensing device 20. However, as will be shown more in detail below, the recesses 80a and 80b may be of many different shapes and need not to be of complementary shape. The protection cavity 100 may be of any shape that allows enclosure about the dispensing device. FIGS. 4a to 4d show an example similar to that of FIGS. 3a to 3d in which the protective enclosure 32 includes enclosure members 60a and 60b with recesses 80a and 80b that are not formed to resemble the dispensing device 20. The protection cavity 100 is instead generally box shaped with rounded corners, and thus, has a volume that is larger than that of the dispensing device 20. The dispensing device 20 is essentially free to move about inside the protection cavity 100. In other examples, however, the movement may be restricted by different support means and or members. Examples of such support means include support members, either as protrusions from the recess walls or as independent members arranged in the protection cavity together with the dispensing device, and will be disclosed in more detail below.

FIGS. 5a to 5d show a similar example to that of FIGS. 3a to 3d including enclosure members 61a and 61b with recesses 81a and 81b. In order to achieve a more firm support of the dispensing device 20 in the protective cavity 100, a plurality of flexible support members 120 are formed in the walls of the recesses. The flexible support members 120 are arranged to define a diameter being smaller than the dispensing device, and when the protective enclosure 32 is closed, the flexible support members are forced about the outer periphery of the dispensing device so that a slight deformation of the support members 120 is achieved. The deformation of the support members consequently results in a peripheral retaining action on the dispensing device limiting movement of the dispenser in the protective cavity. A similar effect can also be achieved by the provision of separate support members of resilient material about the dispensing device, such as a rubber, cardboard or foam ring.

FIGS. 6a to 6d show a similar example to that of FIGS. 5a to 5d comprising rigid enclosure members 62a and 62b with recesses 82a and 82b. In this example, the protective cavity 100 is not shaped so as to resemble the dispensing device 20. Like the example of FIGS. 4a to 4d, it is generally box shaped with rounded corners, and thus, has a larger volume than that of the dispensing device 20. In order to achieve a more firm support of the dispensing device 20 in the protective cavity 100, support members 130a to 130c are formed in the walls of the recesses or potentially separately provided.

Figure 6A:
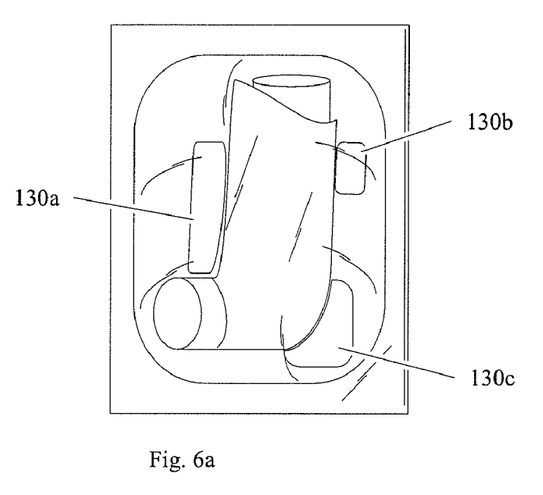
FIGS. 6a to 6d show one example of a protective enclosure and a package.
Figure 6B:
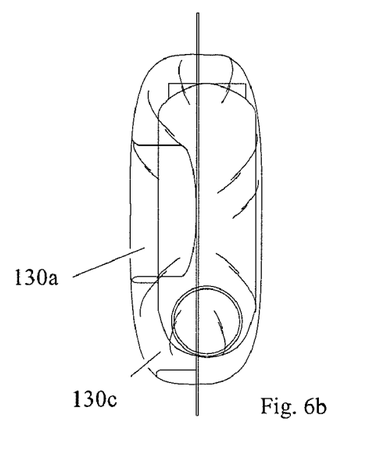
Figure 6C:
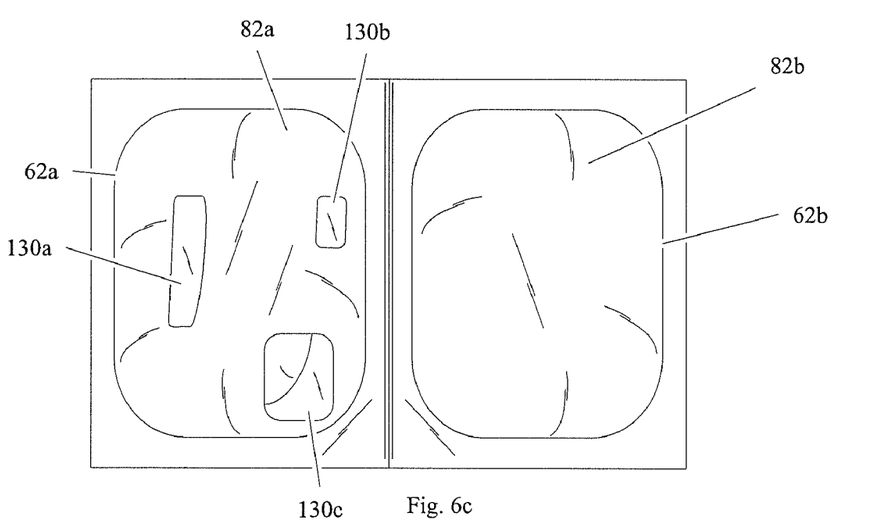
Figure 6D:
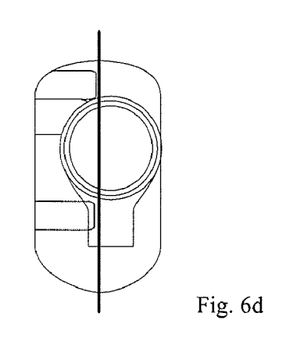
Figure 7A:
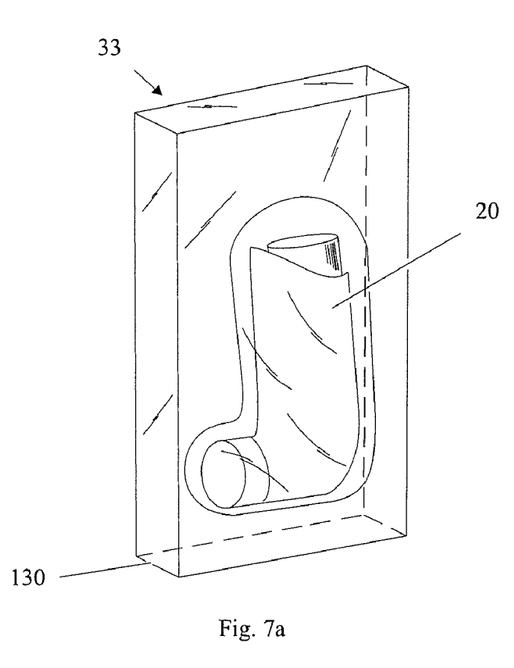
FIGS. 7a to 7c show one example of a protective enclosure and a package.
Figure 7B:
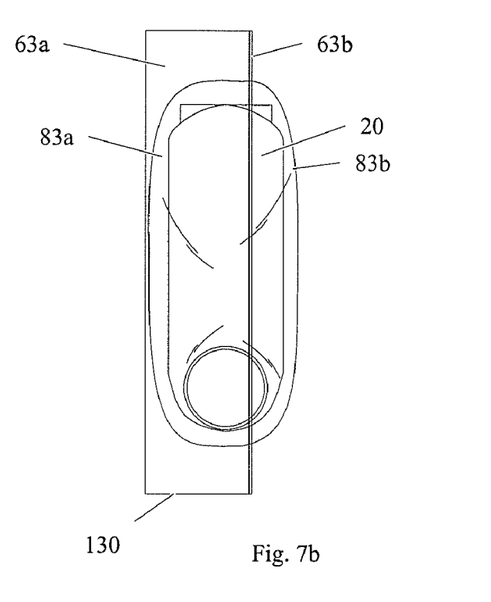
Figure 7C:
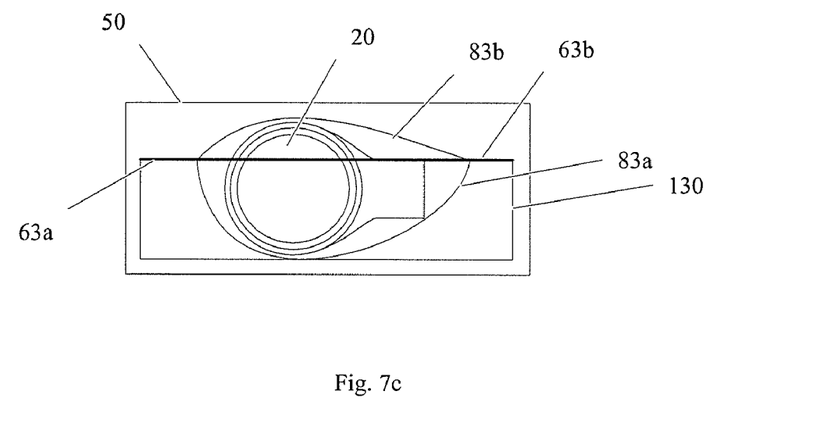

FIGS. 7a to 7c disclose an example in which at least one of the rigid enclosure members 63a and 63b is provided with supportive rim 130 extending from its peripheral edge. The supportive rim provides additional support to the protective enclosure 33. In FIG. 6a, the protective enclosure 30 is shown freestanding without need for an outer box. However, the protective enclosure 30 may also be inserted inside a box 50, in which the supportive rim cooperates with the walls of the box to support the dispensing device in the right position for display purposes and for protecting the same. From FIGS. 7b and 7c it can be seen that the recesses 83a and 83b are non-complementary in order to achieve a wider supportive rim 130 without substantially increasing the over all width of the protective enclosure.

Figure 8A:
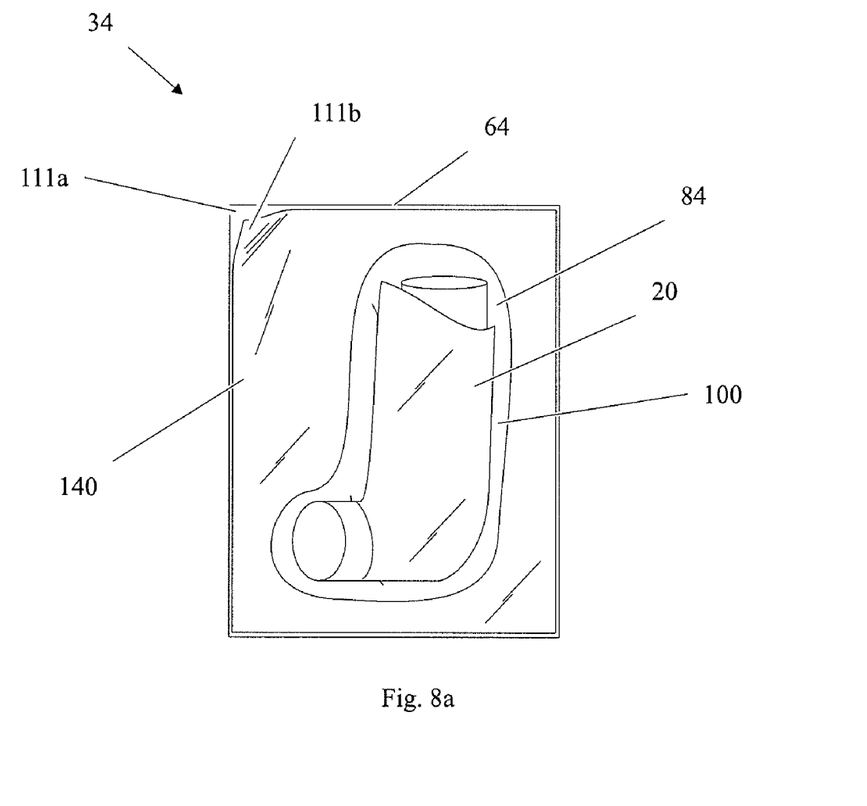
FIGS. 8a to 8c show one example of a protective enclosure and a package.
Figure 8B:
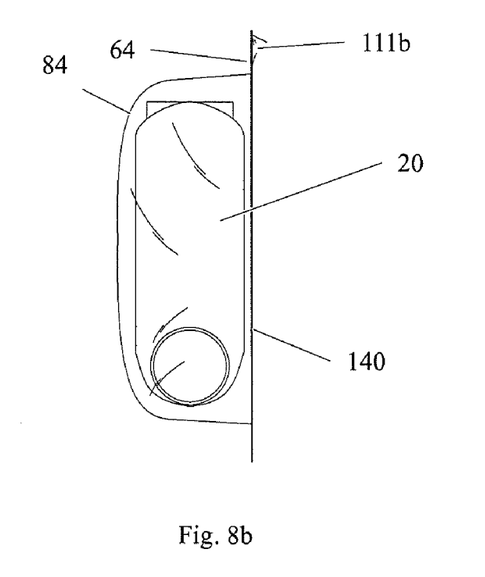
Figure 8C:
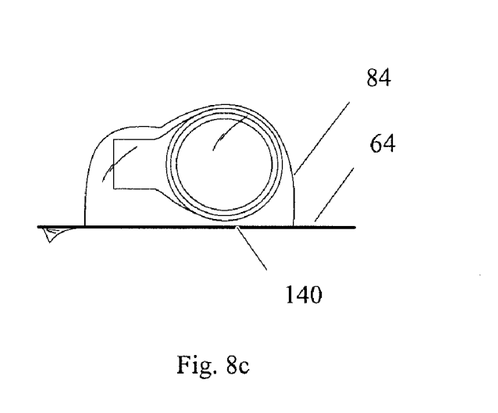

FIGS. 8a to 8c show an example of packaging in which the full depth of the protective enclosure 34 is formed by one recess 84 in a single rigid enclosure member 64. The depth of the recess 84 is essentially equal to the smallest dimension of the dispensing device 20, but the depth and shape of the recess may be correlated to any of the inhaler dimensions, as well as essentially uncorrelated to the dispensing device. A lid member 140 in the form of a flexible sheet is arranged to close the protective enclosure 34. The enclosure type may be referred to as a blister pack due to the similarity to a package for medicament tablets and the like. In this example, the protective enclosure 34 is provided with peel off tabs 111a and 111b. The flexible sheet member is removed by pulling the tab 111b, after which the dispensing device may be removed from the recess 84. In another example, the lid 140 is made of a rigid material and can therefore be referred to as a rigid enclosure member similar to the examples described above, but without a recess. Moreover, the protective enclosure 34 can be provided with a lid 140 that is non-peelable, and therefore must be opened in another way, such as those discussed above.

Figure 9A:
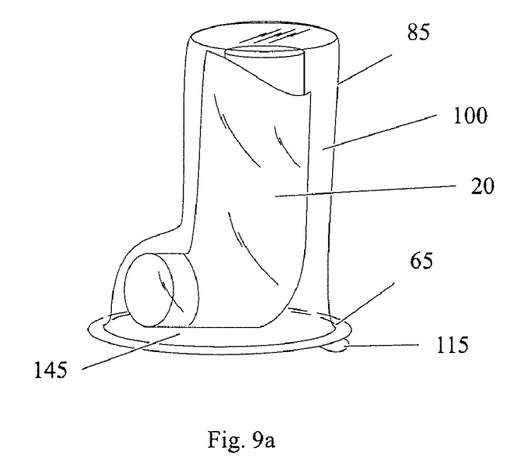
FIGS. 9a to 9c show one example of a protective enclosure and a package.
Figure 9B:
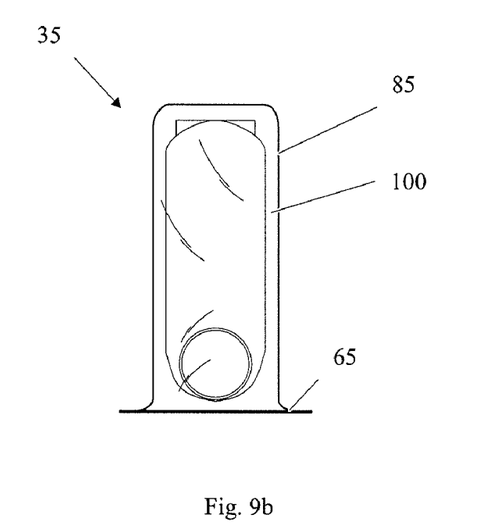
Figure 9C:
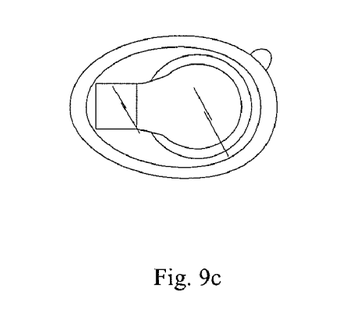

FIGS. 9a to 9c show a similar protective enclosure 35 to that of FIGS. 8a to 8b including a rigid enclosure member 65 with a deep recess 85 and a lid 145, in which the depth of the recess 85 is essentially equal to the largest dimension of the dispensing device. The protective enclosure 35 is given a shape that resemble the inhaler 20, and the protective enclosure 35 is arranged with the lid 145 as bottom surface. The lid 145 serves as a wide stable base/foot. Due to its stable freestanding characteristics, the protective enclosure 35 may be used as a stand alone package 10 without a box. The recess 85 may be given many different shapes which results in new aesthetic possibilities when it comes to packages of this type. Similar to the previous example, the lid 145 may be a peel-off type and provided with a peel-off tab 115, or it can be attached more firmly requiring more invasive methods to open the protective enclosure 35. In another example, the protective enclosure 35 is formed with the lid 145 as top surface and the recess 85 is formed to house the inhaler 20 in a preferred orientation, e.g. with the valve end downwards.

Figure 10A:
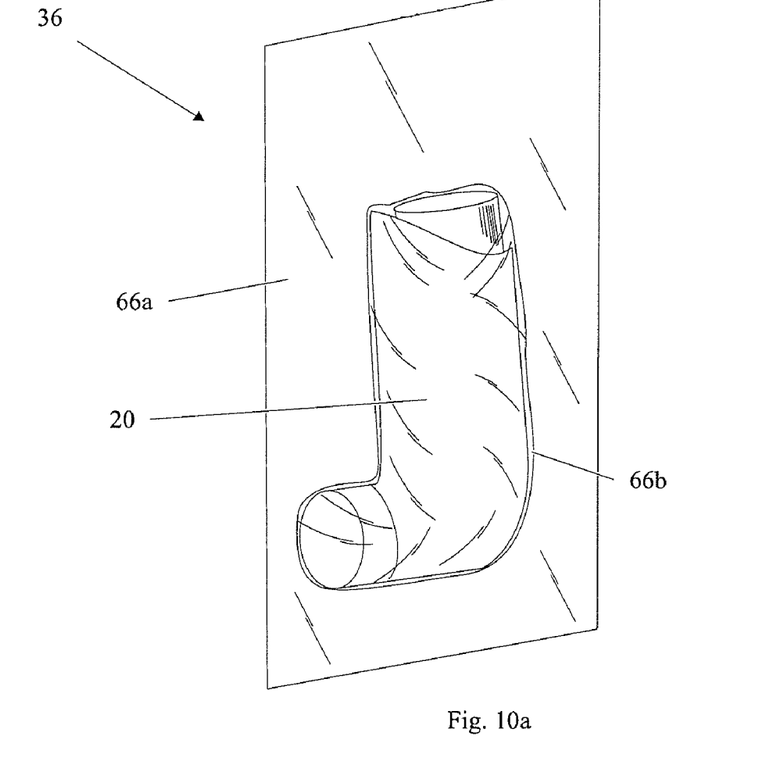
FIGS. 10a and 10b show one example of a protective enclosure and a package.
Figure 10B:
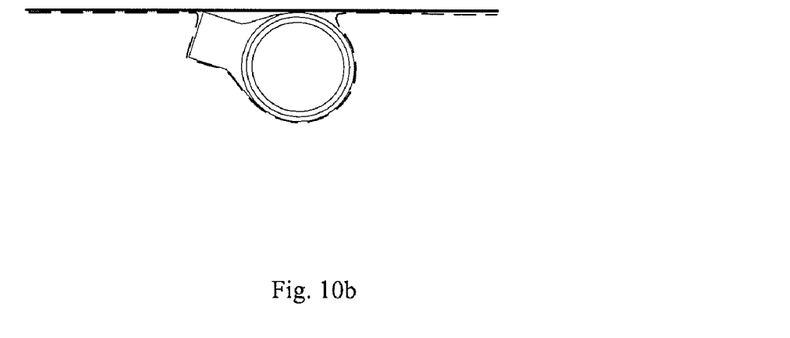

FIGS. 10a and 10b show an example of a protective enclosure 36 including a rigid enclosure member 66a in the form of a flat back plate, and a flexible sheet 66b that is attached closely about the dispensing device 20. The rigid enclosure member 66a provides a rigid back surface to support the dispensing device 20. The flexible sheet 66b is arranged to hold the dispensing device firmly to the back plate 66a. The flexible sheet 66b may be arranged about the dispensing device in any suitable way, such as by heat shrinking, vacuum or the like. The flexible sheet 66b may also hold information sheets in place.

In each of these examples, the protective enclosure may contain a desiccant member or the like to keep a low moisture level in the long term. In the example disclosed in FIG. 11, a desiccant member 160 is arranged in a delimited portion of the protection cavity 100. The desiccant portion of the cavity 100 is formed by delimiting members 170a and 170b. Alternatively, the desiccant member 160 may be placed in the main protection cavity 100 together with the dispensing device 20 or it may be removably attached to the dispensing device 20. Desiccants used in this field are well known in the art, e.g. silica gel sachets, etc., and therefore not described in more detail herein. Moreover, the protection cavity can be formed to house other auxiliary features in addition to or in lieu of the desiccant member 160, e.g. one or more spare mouth pieces, one or more spare canisters, patient information leaflet etc. Such auxiliary features may be arranged in the main cavity 100 or in dedicated sections thereof, like the desiccant portion of FIG. 11.

Figure 12A:
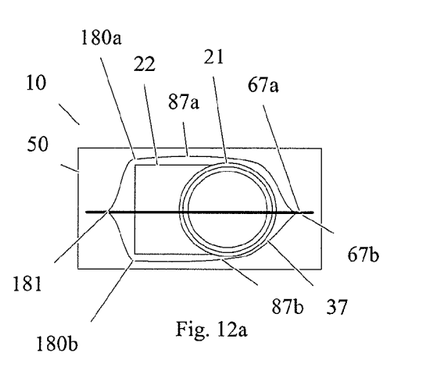
FIGS. 12a and 12b show an example of a protective enclosure and a package.
Figure 12B:
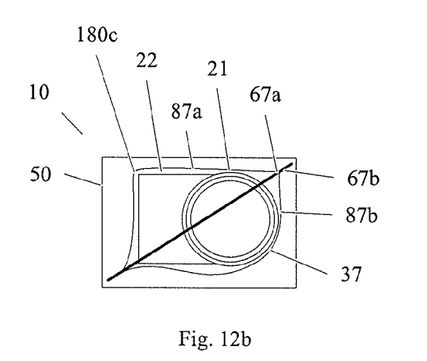

FIGS. 12a and 12b show a top view of a package 10, with a protective enclosure 37 containing a dispensing device 20, arranged in a box 50. For illustrative purposes, the dispensing device of FIGS. 12a and 12b is provided with a wider mouth piece 22 compared to the previously disclosed examples. Similar to the examples above, the dispensing device 20 is a schematic inhaler, essentially comprised of an elongated main body 21 with a mouth piece 22 extending in an essentially transverse direction from the main body 21. In the example shown in FIG. 12a, the protective enclosure 37 includes two rigid enclosure members 67a and 67b with complementary recesses 87a and 87b, respectively. In many of the conventional forming techniques suitable for forming protective enclosures, forming of sharp edges in the recesses present a problem with local material thinning. The thinning of the material is a result of the large deformations involved. Depending on the material selected for the enclosure member, such local thinning of the material may lead to a weakened structural strength and/or impaired moisture or gas protection. In the example shown in FIG. 12a, the wide mouth piece 22 gives rise to one sharp edge 180a and 180b in each recess 87a and 87b, respectively. Moreover, the sharp edges are preferably formed as close to the rim 181 of the enclosure members 67a and 67b as possible to save package volume. In order to reduce the occurrence of sharp edges, the protective enclosure 37 of FIG. 12b includes two rigid enclosure members 67a and 67b that are attached to each other in a plane that is essentially parallel with the longitudinal direction of the main body, and diagonal to the extension direction of the mouth piece. The enclosure members 67a and 67b have recesses 87a and 87b, respectively, that are non-complementary in that essentially the whole mouth piece is housed in the recess 87a and a large portion of the main body is housed in recess 87b. This diagonal arrangement minimizes the occurrence of sharp edges 180c in the recesses 87a and 87b in the case of a protection cavity that resembles the shape of an inhaler. Moreover, the diagonal enclosure arrangement leads to a more volume efficient package 10 because the rim 70 is placed in the corners of the box 50. A more volume efficient package leads to savings in the transportation of packages. This arrangement lends strength to the package in that only one corner or edge 180c is produced, thereby reducing areas of thinning or weakness.

A number of examples of the invention have been described. Nevertheless, it will be understood that various modifications may be made without departing from the spirit and scope of the invention. Accordingly, other examples are within the scope of the following claims.

What is claimed is:

1. An inhaler package comprising a protective enclosure containing an inhaler, wherein the protective enclosure comprises:
    a first rigid enclosure member and a second rigid enclosure member, the first and second rigid enclosure members being attached to each other;
    a first delimiting member formed on the first rigid enclosure member; and
    a second delimiting member formed on the second rigid enclosure member;
    wherein each of the first and second rigid enclosure members defines a recess to house a respective section of the inhaler;
    wherein the first and second rigid enclosure members comprise first and second opening tabs, respectively; and
    wherein the first and second delimiting members form a delimited portion, the delimited portion adapted to receive at least one auxiliary feature, the auxiliary feature being selected from a desiccant member, a patient information leaflet, a spare mouth piece, or a spare canister.

2. The inhaler package of claim 1 wherein each recess has a shape resembling the respective section of the inhaler.

3. The inhaler package of claim 2 wherein the inhaler has an elongated main body and a mouth piece extending in an essentially transverse direction with respect to the main body, and wherein the section of the inhaler housed within the recess defined by one of the two rigid enclosure members comprises essentially the whole mouth piece.

4. The inhaler package of claim 3 wherein the two rigid enclosure members are attached to each other in a plane that is essentially parallel with a longitudinal direction of the main body, and diagonal to the transverse direction in which the mouth piece extends.

5. The inhaler package of claim 1 wherein the two rigid members are formed from one sheet of rigid material that is folded.

6. The inhaler package of claim 1 further comprising at least one support member arranged to support the inhaler.

7. The inhaler package of claim 6 wherein the support member is integrally formed in the recess of at least one of the two rigid enclosure members.

8. The inhaler package of claim 1 further comprising one or more auxiliary features selected from a desiccant member, a patient information leaflet, a spare mouth piece, or a spare canister, wherein the auxiliary feature is received in the delimited portion.

9. The inhaler package of claim 1 wherein the protective enclosure is arranged in a box.

10. The inhaler package of claim 1 wherein the rigid enclosure member is coated with a functional layer comprising a barrier coating reducing gas and moisture permeability of the protective enclosure.

11. The inhaler package of claim 1 wherein the rigid enclosure member is coated with a functional layer comprising a radiation protection coating.

* * * * *